United States Patent
Storrie et al.

(10) Patent No.: US 6,631,283 B2
(45) Date of Patent: Oct. 7, 2003

(54) B/B-LIKE FRAGMENT TARGETING FOR THE PURPOSES OF PHOTODYNAMIC THERAPY AND MEDICAL IMAGING

(75) Inventors: Brian Storrie, Blacksburg, VA (US); Maria Tarrago-Trani, Blacksburg, VA (US); Sam English, Roanoke, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 119 days.

(21) Appl. No.: 09/894,896

(22) Filed: Jun. 29, 2001

(65) Prior Publication Data

US 2002/0090340 A1 Jul. 11, 2002

Related U.S. Application Data

(60) Provisional application No. 60/248,206, filed on Nov. 15, 2000.

(51) Int. Cl.[7] .................................................. A61B 5/05
(52) U.S. Cl. ................................ 600/407; 600/1; 600/3; 128/898
(58) Field of Search ................................ 600/407, 1, 3, 600/7; 128/898; 606/2; 604/19, 20; 514/2; 424/133.1, 1.11, 9.1, 155.1, 423

(56) References Cited

U.S. PATENT DOCUMENTS

| | | | | |
|---|---|---|---|---|
| 5,877,305 A | * | 3/1999 | Huston et al. | 424/133.1 |
| 6,051,207 A | * | 4/2000 | Klaveness et al. | 424/9.1 |
| 6,264,914 B1 | * | 7/2001 | Klaveness et al. | 424/1.11 |
| 6,270,472 B1 | * | 8/2001 | Antaki et al. | 600/7 |
| 6,433,149 B1 | * | 8/2002 | Blaschuk et al. | 424/155.1 |
| 6,524,552 B2 | * | 2/2003 | Klaveness et al. | 424/1.11 |

* cited by examiner

*Primary Examiner*—Teresa Walberg
*Assistant Examiner*—Fadi H. Dahbour
(74) *Attorney, Agent, or Firm*—Whitham, Curtis & Christofferson, P.C.

(57) ABSTRACT

The invention provides compositions and methods for use in delivering a substance of interest to a targeted cell. The substance of interest is associated with a targeting fragment of a toxin molecule or a lectin that specifically binds to a cell surface receptor, such as the B subunit of an A/B type toxin molecule. The substance of interest may be a photosensitizing agent, in which case the cell (e.g. a cancer cell) may be killed by exposure to light after delivery of the agent. Alternatively, the substance of interest may be a visualizing agent that enhances visualization of the targeted cell.

14 Claims, 10 Drawing Sheets

 
*Figure 5A*  *Figure 5B*

B/B-LIKE FRAGMENT TARGETING FOR THE PURPOSES OF PHOTODYNAMIC THERAPY AND MEDICAL IMAGING

This application claims the benefit of Provisional Application No. 60/248,206, filed Nov. 15, 2000.

BACKGROUND OF THE INVENTION

1. Field of the Invention

The invention generally relates to the use of a targeting fragment of a toxin or lectin molecule for the delivery of a substance of interest to cells. In particular, the invention provides a composition comprising a targeting fragment of a toxin molecule and a substance of interest, and methods for use of the composition. More particularly, the substance of interest may be a photosensitizing agent for use in targeted cell killing, or a visualizing agent for use in identifying cell surface receptors of interest.

2. Description of Related Art

The "holy grail" of research in the battle against cancer has been the development of a magic bullet to selectively kill cancerous cells while leaving normal cells untouched. Standard, therapeutic approaches to the treatment of cancer include surgery to remove the cancerous tissue (if the tumor is well defined and localized), radiotherapy, chemotherapy or combinations of these methods. Frequently, when a cancerous tumor is removed, a significant portion of surrounding tissue is also removed to ensure that the majority of cancerous cells are eliminated. In some cases, an entire organ is removed, even though portions of the organ are still healthy. In spite of such radical procedures, cancer cells may spill into body cavities and remain behind to proliferate. Further, portions of a tumor may be difficult to discern or difficult to access. The ability to accurately target cancerous cells for destruction while leaving normal, healthy tissue intact would be a major step forward in the treatment of this disease.

One form of therapy that is currently gaining acceptance for the treatment of hyperproliferating tissues is photodynamic therapy (PDT). Based on the discovery made over years ago that rapidly growing cells treated with certain chemicals will die when exposed to light, PDT is currently being used to treat several different types of cancers and non-malignant lesions. There appears to be a selective affinity and retention of photosensitizers in hyperproliferating tissue. Commonly, a patient is injected with a photosensitizer (PS) molecule that spreads throughout the body. There is then a waiting period during which the PS molecules accumulate in the target tissue, and are eliminated from most non-target tissue. Light is then used to illuminate a mass of tumor cells and activate the PS molecules to produce singlet oxygen, thereby killing cells and tissue in the area. The use of PDT to treat esophageal cancer, lung cancer and macular degeneration is currently being evaluated in clinical trials. One of the theoretical advantages of PDT is that tissues unexposed to light will not be affected. However, in reality, the rate of clearance of the photosensitizer from normal tissue is highly variable. Thus, while success rates of treatment with PDT are so far impressive, deleterious side effects such as skin sensitivity to light for four to six weeks have been observed. In addition, inflammation of the treatment site resulting in shortness of breath and coughing has been observed as a result of PDT treatment of lung and esophageal cancers.

Attempts have been made to optimize PDT treatments. U.S. Pat. No. 6,058,937 to Dorion et al., the disclosure of which is incorporated herein by reference, presents a method for shortening the waiting period after administration of PDT to a tissue. The technique is limited, however, to highly vascularized tissue. Rather than destroying the tissue itself, PDT is used to destroy the vasculature that nourishes the tissue and thus indirectly causes tissue death. The majority of molecules do not readily penetrate cell membranes. Methods for introducing molecules of interest into the cytosol of living cells are disclosed in U.S. Pat. No. 5,876,989 to Berg et al., the disclosure of which is incorporated herein by reference. The molecules to be released into the cell's cytosol are first taken up in endosomes, lysosomes or other cell compartments together with a photosensitizing compound. Light activation of the photosensitizing compound is then used to rupture the membranes of the cell compartments. The contents of the ruptured compartments (including the molecule of interest) are released into the cell cytosol without killing the majority of the cells. This invention thus utilizes PDT as a mechanism for releasing a drug (such as gelonin, a ribosome inactivating protein) from endosomes/lysomes to the cell compartment where the drug is effective (cytosol). The method does not provide a method of cell killing by PDT.

Kraus et al. in U.S. Pat. No. 6,160,024 describe chemical linkers to connect an energy emitting compound to a photosensitizing molecule, thereby providing an internal chemically-activated light source for activation of the photosensitizer. The method was employed to destroy virus-infected or tumor cells. However, this and other known PDT methods generally lack specificity. Their use results in whole body sensitization to illumination and the attendant side effects.

A need, therefore, exists for a way to enhance the specificity of PDT in order to avoid whole-body light sensitivity.

In order to enhance the specificity of cancer therapies, researchers have attempted to take advantage of the many biochemical and physiological changes that occur during cancer cell transformation. Some of these changes include the presence of cell-surface molecules when cells become cancerous. This has led to the use of antibodies coupled with toxic compounds to selectively bind to the surface of cancerous cells thereby killing those cells. However, this approach also has limitations that include the heterogeneous uptake of the toxin by the tumor cells, the slow elimination of the antibody-toxin complex from the blood system, and the cross-reactivity of the antibody with normal tissue.

The differential expression of many cell-surface molecules in human cancerous cells has been well studied and thoroughly documented. One such molecule is globotriaosylceramide (also known as $Gb_3$, CD77 and $p^k$ antigen). The $Gb_3$ glycosphingolipid is normally expressed in several tissues including intestinal epithelium, kidney epithelium, and endothelial cells, in addition to being found in human milk as a glycolipid. $Gb_3$ is also expressed in a fraction of germinal center B lymphocytes, and traces of $Gb_3$ are found in red blood cell membranes of most individuals. $Gb_3$ is strongly expressed in the red blood cell membranes of $p^k$ blood type individuals (0.01% of the population). The over-expression of this cell-surface receptor has been documented in ovarian cancer, Burkitt's lymphoma (non-Hodgkin's lymphoma), breast cancer, brain cancer, gastric cancer, and testicular cancer. It would not be unreasonable to predict that the over-expression of $Gb_3$ may occur in many other types of cancer, as well.

The $Gb_3$ receptor (intestinal) is targeted by the bacterial toxin proteins belonging to the verotoxin family of bacteriotoxins that includes the Shiga toxins and Shiga-like toxins. Bacterial (*Shigella dysenteriae* and *Escherichia coli*) production of these toxins leads to disorders such as food poisoning, dysentery, hemorrhagic colitis, and hemolytic uremic syndrome. It is not the actual bacterial infection, but the production of the toxin molecules that leads to the disease symptoms. The bacteriotoxins, both Shiga and Shiga-like, are comprised of two protein components, a catalytic A subunit and a pentameric B subunit. The catalytic A subunit is a potent N-glycosidase that inhibits protein synthesis once inside a cell. The B subunit array is responsible for targeting specific cells expressing $Gb_3$ on their surface by recognizing and binding the $Gb_3$ receptor. Several issued patents take advantage of the targeted specificity of verotoxins to localized positions on cancerous cells.

Verotoxin 1, or the pentameric B subunit of verotoxin 1, administered in a non-lethal amount has been effective in treating mammalian neoplasia, including ovarian, brain, breast, and skin cancers as described, for example, in Lingwood et al., U.S. Pat. No. 5,968,894, the disclosure of which is incorporated herein by reference.

Gariepy in U.S. Pat. No. 5,801,145, the disclosure of which is incorporated herein by reference, describes the treatment of non-Hodgkin's lymphomas by a related ex vivo method. Taking advantage of the fact that Shiga toxin or Shiga-like toxin-1 selectively binds to CD77+ cells, according to this method bone marrow cells are treated with the toxins to specifically kill CD77+ cells prior to a bone marrow transplant.

While some of these methods utilize cell targeting via specific cell surface receptors, they lack the benefits of PDT.

An indispensable component of cancer treatment protocols is the ability to detect and locate, i.e. to visualize tumors. The noninvasive visualization of cancerous tumors is technically challenging and has led to the development and application of numerous modalities. These include X-ray, CT scan, nuclear scan, PET scan, MRI, ultrasound and numerous modifications that are used to visualize tumors. These techniques are used routinely for general biomedical imaging with each having distinct advantages and disadvantages. Overall, the most significant disadvantage of these techniques is the lack of sensitivity to detect small abnormalities. As such, a high level of skilled expertise is required by personnel to identify a small cancerous tumor. The detection and identification of a cancerous growth is paramount to achieving a positive outcome for the patient. The ability to readily distinguish between cancerous cells and normal cells would be of tremendous benefit to an oncologist or clinician.

Thus, there is also an existing need for a method that allows specific detection, localization, and visualization of cancerous cells. A methodology that provides noninvasive imaging of tumors and simple visual discrimination of cancerous versus normal cells would be highly beneficial.

Therefore, the principle need is for a vehicle and method for delivery of substances of interest specifically to targeted cells that provides all of the above referenced advantages without the disadvantages associated with each taken individually.

SUMMARY OF THE INVENTION

It is a principle objective of the present invention to provide a methodology of delivering molecules of interest to cells. The method involves associating a substance of interest with a targeting fragment of a toxin or lectin molecule. The targeting fragment mediates the cellular delivery and internalization of the substance of interest. The substance of interest will be internalized by cells possessing the cell surface receptor for which the targeting fragment is specific.

In one aspect, the present invention targets a cell surface receptor (CD77, $Gb_3$) identified as being over expressed in ovarian cancer cells, Burkitt's lymphoma cells, breast cancer cells, gastric cancer cells, and testicular cancer cells. The receptor is naturally expressed in intestinal epithelium, kidney epithelium and endothelial cells, in addition to being found in human milk. This receptor is naturally targeted by the B subunit of the bacterial protein SLT. Once bound to the receptor via the B subunit, the entire protein is internalized by the cell. The B subunit thus functions to "deliver" the catalytic A subunit of SLT to the cell. By coupling a substance of interest to the B subunit of SLT (SLT-B) in lieu of the A subunit, it is likewise possible to deliver the substance of interest to cells possessing the $Gb_3$ receptor.

In one embodiment of the present invention, the substance of interest is a photosensitizing agent. For example, the photosensitizing agent chlorin e6 (Ce6) has been well studied and used as a model system for photodynamic therapy. The instant invention describes coupling Ce6 with SLT-B to affect cell killing using light.

In one embodiment of the instant invention, the substance of interest that is attached to the targeting fragment and delivered to a target cell is a visualizing agent. The resulting targeting fragment/visualizing agent composition would be useful for identifying cell surface receptors of interest in patients and clinical samples. This application includes the identification of cell surface receptors in both pathogenic (e.g. cancerous) tissue and normal tissue. Examples of suitable clinical samples include but are not limited to biopsy samples, blood samples, bone marrow samples, and the like.

For the practice of this aspect of the invention, a composition comprising a targeting fragment of a toxin or lectin molecule and a visualizing agent are provided to a patient, or to a clinical sample, and the cell surface receptor of interest is then located in the patient or the clinical sample by imaging the visualizing agent after the targeting fragment has bound to the receptor of interest. Those of skill in the art will recognize that many types of imaging exist that could be utilized in the practice of this aspect of the invention, including but not limited to such procedures as scintigraphy (nuclear scanning), x-ray or CT scans, magnetic resonance imaging (MRI), and the like. Any suitable type of imaging may be utilized in the practice of the present invention so long as the visualizing agent that is delivered via the targeting fragment can be detected.

In one embodiment of the present invention, the cell surface receptors that are identified by the practice of the present invention are associated with cancer cells and identification of the cell surface receptors allows visualization of the cancer cells. However, those of skill in the art will recognize that the visualization of cells displaying such receptors would be advantageous in many circumstances. Examples include but are not limited to the visualization of tissues (normal or diseased) prior to or during surgical procedures, localization of specific cell types, monitoring cell location, and the like. The method of the present invention may be utilized to identify any cell surface receptor of interest, so long as the receptor binds with specificity to a targeting fragment of a toxin or lectin molecule.

The practice of this aspect of the present invention would provide a distinct advantage in, for example, identifying and locating tumors or other cancerous cells and thus for planning treatment protocols. The method could aid in the assessment of metastasis, or be useful during surgery to remove tumors. For example, the practice of the method of the present invention would render cancerous tissues visible and distinguishable from normal tissue. It would thus be possible to be more conservative with respect to removal of tissue that is not cancerous, thereby minimizing the loss of healthy tissue by the patient.

It is yet another objective of the present invention to provide a methodology for the direct visualization of cancerous cells by complexing a fluorescent molecule to the B fragment, illuminating with an appropriate light and observing the light emitted. This methodology would be used, for example, during biopsy or surgical procedures.

Another objective of the present invention to provide a predictable method of detecting normal expression patterns in intestinal and other tissues. Because the $Gb_3$ receptor is expressed in tissue other than tumor cells, there would be areas of localization of a conjugate regardless of the presence of tumor cells. However, the localization in intestinal tissue or elsewhere would be predictable based upon known normal expression patterns. This embodiment of the invention could be used for imaging of normal intestinal, kidney and endothelial tissues (vasculature) for example to detect changes in expression that may result from physiological changes associated with conditions such as disease, pregnancy, administration of drugs, aging, etc.

BRIEF DESCRIPTION OF THE DRAWINGS

FIGS. 5A and B. Ce6-SLTB Localizes to Mitochondria and Secretory Organelles: Colocalization of Mito Tracker® Green FM and Ce6-SLTB in Vero cells. Panel A: MitoTracker® Green FM fluorescence; Panel B: Ce6 fluorescence.

DETAILED DESCRIPTION OF THE PREFERRED EMBODIMENTS OF THE INVENTION

Figure 1A:
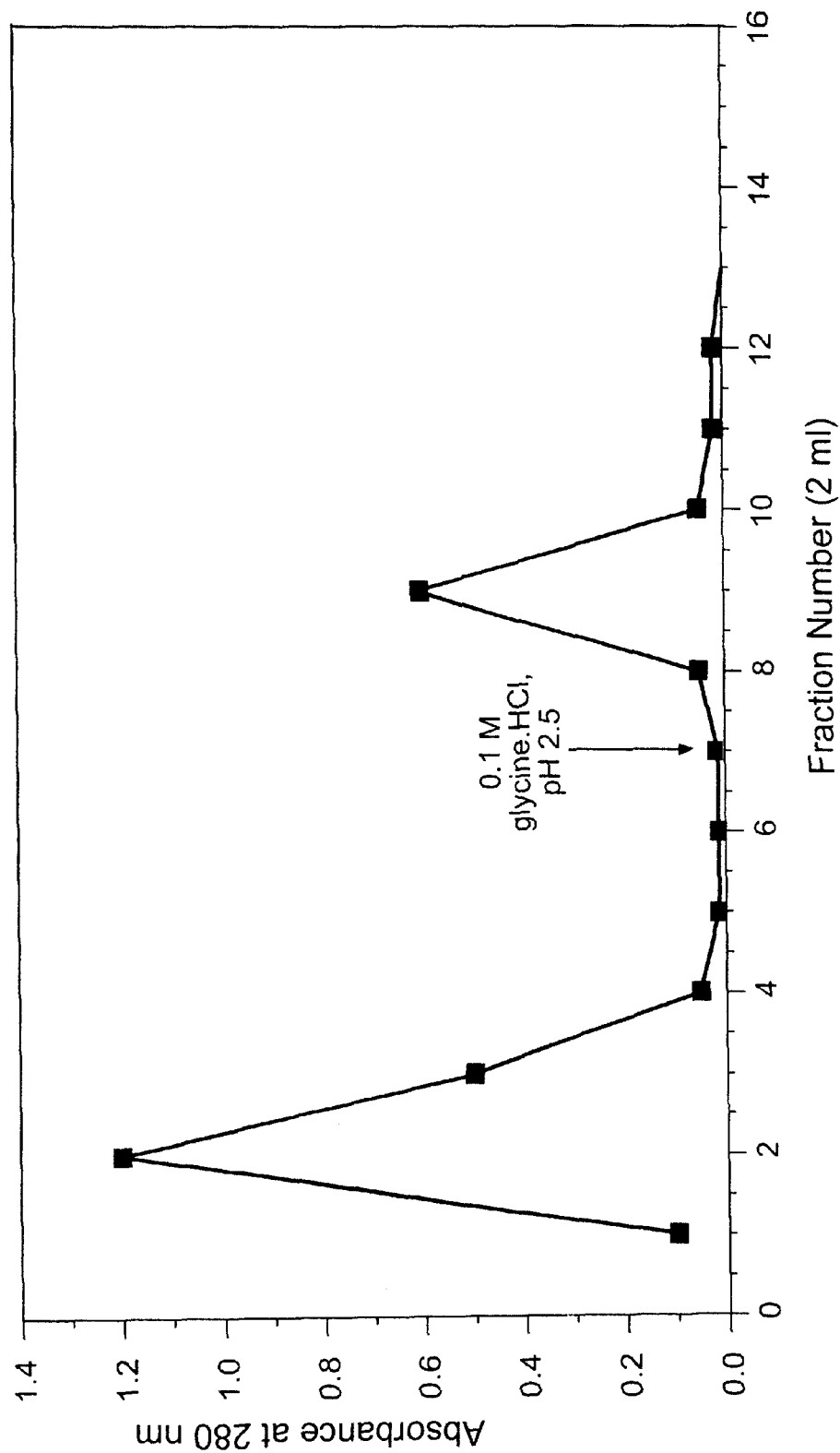
FIGS. 1A and B. Affinity chromatography. Galabiose-agarose affinity chromatography of *Vibrio Cholerae* 0395-N1/pSBC54 periplasmic extract (panel A), and Cy3-SLTB used as standard (panel B).
Figure 1B:
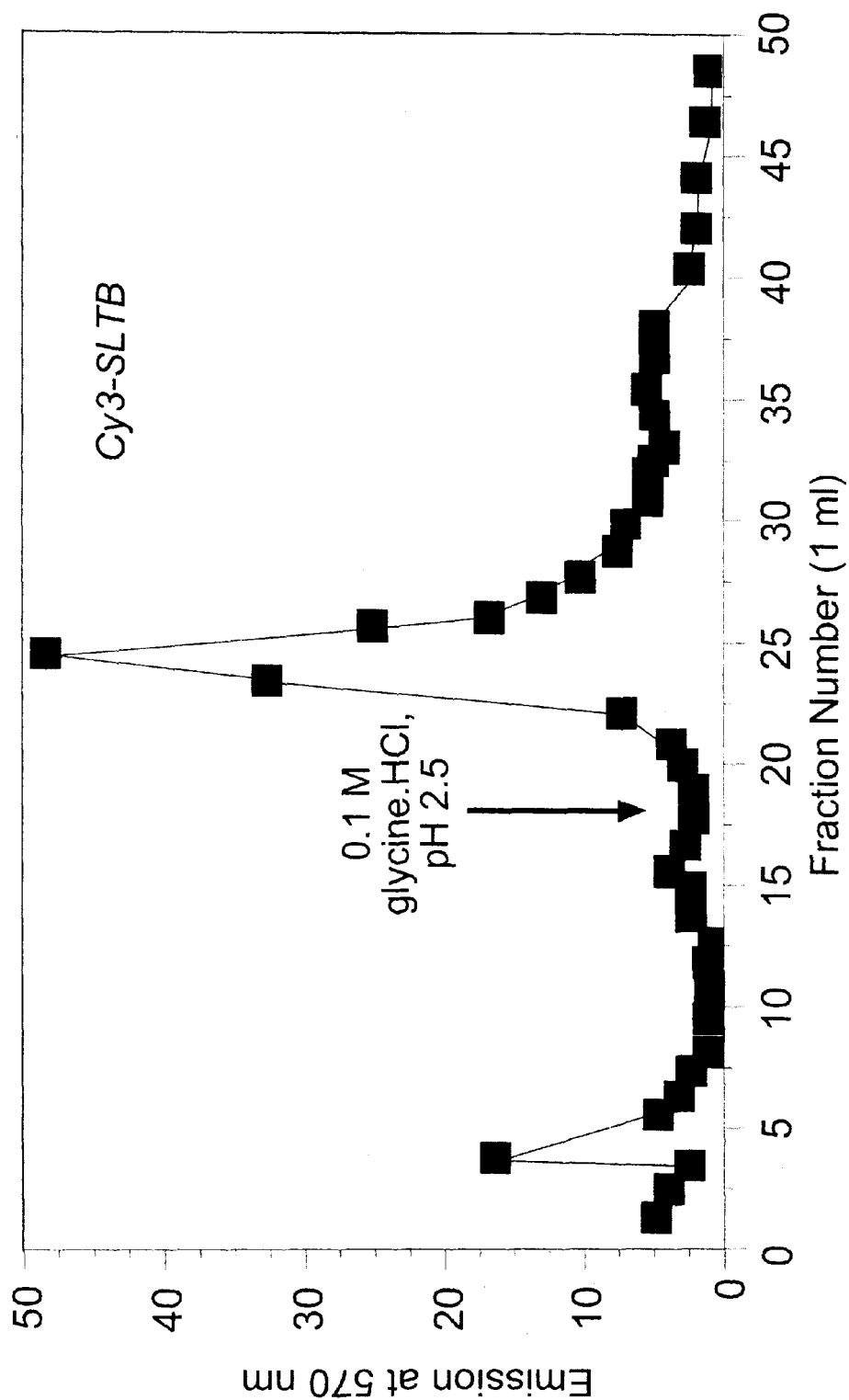
Figure 2:
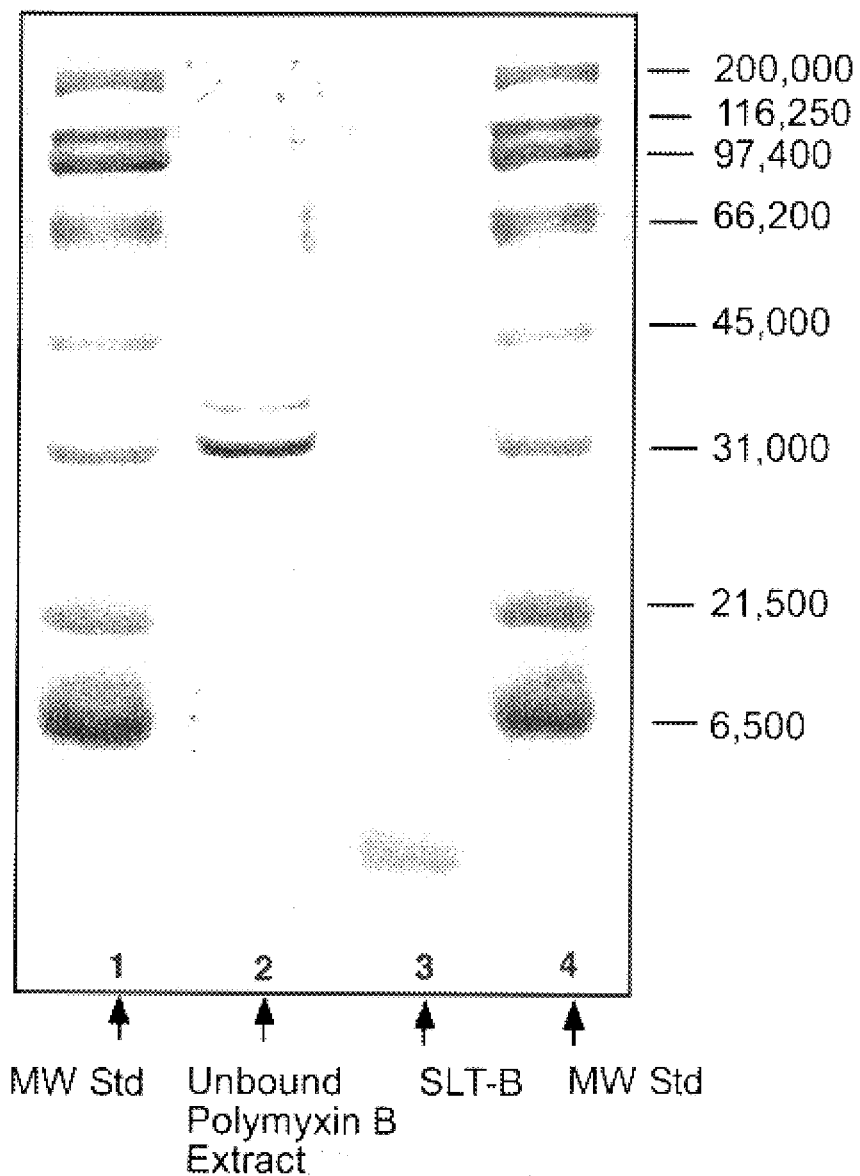
FIG. 2. SDS-PAGE gel of SLTB. Electrophoresis was run on 15% polyacrylamide gels at a constant current of 20 mAmps. Lanes 1 and 4 represent molecular weight standards; lane 2 represents the unbound polymyxin B extract; lane 3 represents the Shiga-like toxin B fragment (SLTB) after affinity chromatography purification.
Figure 3:
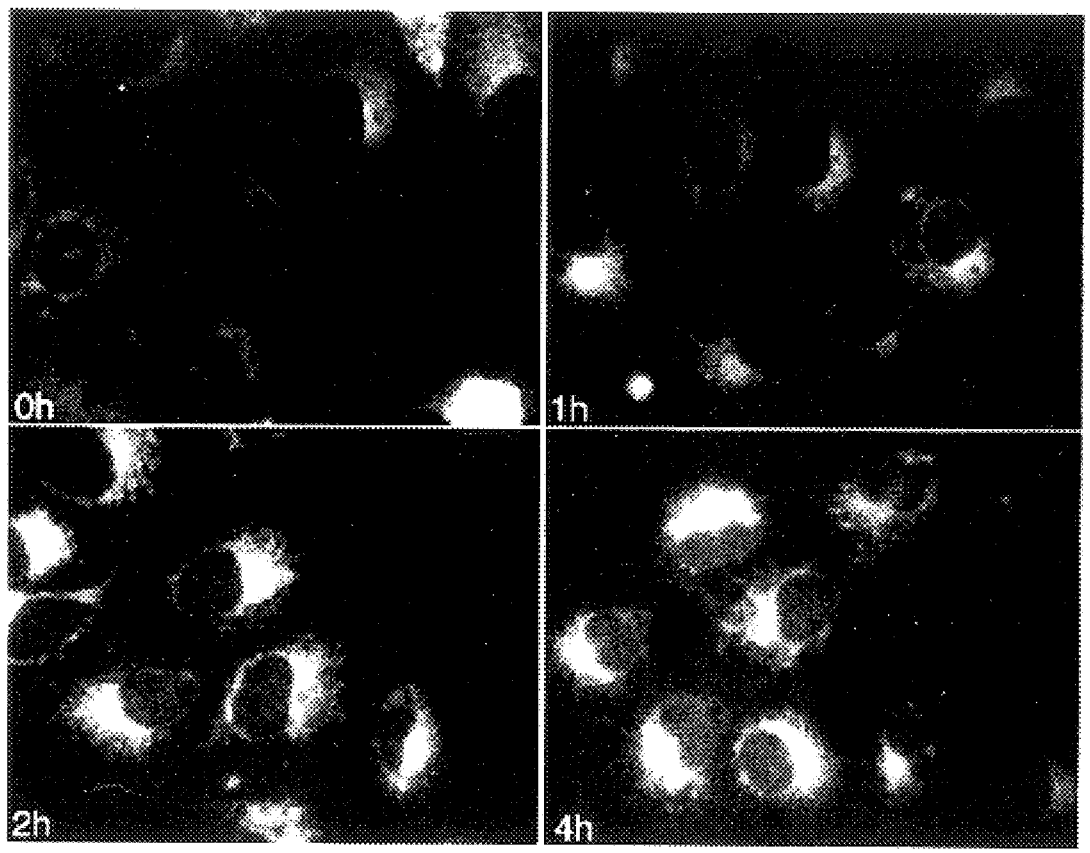
FIG. 3. Binding and uptake of Ce6-SLTB conjugate in Vero cells. Fluorescence images of Vero cells incubated with mixed (covalent and absorbed) Ce6-SLTB conjugate at 0, 1, 2, and 4 hours of chase.
Figure 4:
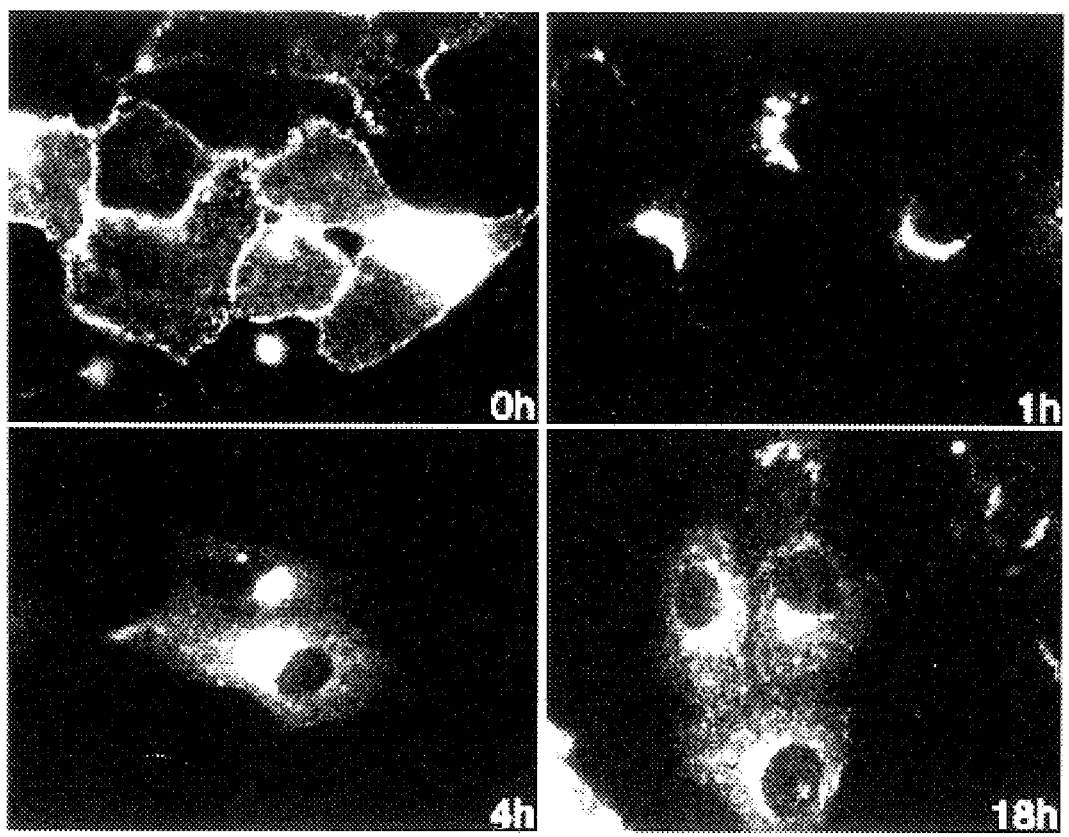
FIG. 4. Binding and uptake of Cy3-SLTB in Vero cells. Fluorescence images of Vero cells incubated with Cy3-SLTB at 0, 1, 4, and 18 hours of chase.

Applicant's have discovered methods for selectively delivering a substance of interest to targeted cells. The method involves providing to cells a composition comprising two moieties: 1) a targeting fragment of a toxin or lectin molecule and 2) the substance of interest. By "a targeting fragment of a toxin or lectin molecule" we mean the portion of a toxin or lectin molecule that binds with specificity to a receptor located on the surface of a cell, i.e. the targeting fragment is a ligand for the cell surface receptor. Such a targeting portion of a molecule may also be termed a "fragment" or "subunit" of the molecule. Those of skill in the art will recognize that in some cases, the portion of a toxin or lectin molecule suitable for use in the present invention will be a subunit of a multimeric (oligomeric) molecule, the subunit being encoded by a gene that is distinct from that of the other components of the holotoxin or lectin. The holotoxin or lectin is assembled post-translationally, and the targeting subunit may be obtained in a variety of manners, including isolation of the holotoxin or lectin followed by separation of subunit components, cloning of the DNA encoding the targeting subunit and production via recombinant DNA technology, synthetic production of the subunit by peptide synthesis, and the like. In other cases, the targeting portion of a toxin or lectin molecule may be a "fragment" of the entire toxin or lectin molecule, i.e. the part of the polypeptide chain that represents the targeting portion is contiguous with the rest of the molecule and forms part of the toxin or lectin polypeptide chain. In this case, the entire toxin molecule is translated from a single mRNA (as the result of being encoded by a single gene, or as the result of mRNA splicing). The "targeting fragment" may be obtained as a distinct entity for use in the present invention by such methods as, for example, proteolysis of the toxin molecule, cloning of the DNA that encodes the targeting portion of the toxin polypeptide, synthetic production of the targeting fragment by peptide synthesis, and the like. In addition, the "targeting fragment" itself may be comprised of a single polypeptide chain, or of multiple polypeptide chains associated with each other e.g. by covalent, hydrophobic, or ionic interactions, and the like, i.e. the targeting fragment may, in and of itself, be oligomeric.

By "binds with specificity" we mean that the Kd will be in the range of approximately $10^{-10}$ to $10^{-20}$ $M^{-1}$, and more preferably in the range of approximately $10^{-12}$ to $10^{-17}$ $M^{-1}$. By "substance of interest" we mean a substance that is associated with the targeting fragment and that possesses a desired activity. For example, the substance of interest may be a photosensitizing agent or a visualizing agent. The association of the substance of interest with the targeting fragment allows delivery of the substance of interest to the targeted cell. Without being bound by theory, it is believed that the associated substance/targeting fragment conjugate binds to the cell surface receptor of a targeted cell via the targeting fragment. Following binding, the substance of interest is "piggy-backed" into the cell via the targeting fragment of the conjugate by receptor mediated endocytosis. However, for some purposes, the conjugate may function equally well by binding to the cell surface receptor without internalization. Further, the substance of interest may enter the cell by means other than receptor mediated endocytosis, e.g. by passive diffusion.

In some embodiments of the instant invention, the targeting fragment originates from a toxin molecule. In other embodiments, the targeting fragment originates from a lectin molecule. The name lectin comes from the Latin word legere, which means "to select". The term was created by W. C. Boyd to designate plant agglutinins that had blood group specificity (Kilpatrick, 2000). The biochemical basis of the lectin agglutination reaction with erythrocytes and other cells is the recognition and binding of the lectin to terminal and internal carbohydrate structures in cell surface glycoconjugates. Lectins are widespread in nature and are not limited to plants, they are found in animals, bacteria and viruses. A definition that is broadly accepted in the field describes lectins as carbohydrate-binding proteins that are not involved in carbohydrate metabolism and do not belong to any of the main immunoglobulin classes (Kilpatrick, 2000).

In some embodiments of the instant invention, the substance of interest may be, for example, a photosensitizing agent. In this case, the conjugate compositions of the instant invention may be used to carry out selective cell killing by delivering the photosensitizing agent to a cell where it is then internalized by the cell. Subsequent exposure of the cell to light activates the photosensitizing agent and causes cell damage or death. The cells to which the composition of the present invention are provided and which are subsequently exposed to light may be either in vivo or ex vivo. In other embodiments of the instant invention, the substance of interest may be, for example, a visualizing agent. The visualizing agent is delivered to a cell via the conjugate. The conjugate is bound to the cell via the targeting fragment moiety, thus providing a method to identify cell surface receptors of interest. (Only those cells possessing the receptor of interest will bind the conjugate). Use of the method permits visualization by various imaging techniques of cells which posses cell surface receptors that bind the targeting fragment moiety of the conjugate. Cells to which the visualizing agent are delivered and which are subsequently imaged may be either in vivo or ex vivo.

Those of skill in the art will recognize that many types of toxins and lectins exist, the targeting fragments of which may be employed in the composition and methods of the present invention. Potentially useful toxins and lectins include but are not limited to those presented in Table 1.

TABLE 1

Protein Toxins that Possess Cell Surface Receptor Targeting Fragments

| Toxin Name | Origin | Cell Surface Receptor | Potential Target |
| --- | --- | --- | --- |
| Abrin | A/B plant toxin | non-reducing terminal galactose-containing glycoconjugates | sarcomas, leukemias |
| A/B heat labile toxins | Escherichia coli | gangliosides GM1, GD1b, GM2 | brain, nerve, intestinal tissue |
| Botulinum toxin | Clostridium botulinum (bacterial) | gangliosides GT1b, GQ1b | brain and nerve tissue |

TABLE 1-continued

Protein Toxins that Possess Cell Surface Receptor Targeting Fragments

| Toxin Name | Origin | Cell Surface Receptor | Potential Target |
| --- | --- | --- | --- |
| Cholera toxin | Vibrio cholerae (bacterial) | ganglioside GM1 | brain and nerve tissue |
| Helix pomatia | Plant lectin | terminal alpha-GalNAc | breast cancer |
| Jacalin or Jackfruit | Plant lectin | TF antigen, Gal-beta1-3/4Glc/GalNAc-alpha terminal epitope of glycoconjugates | gastric, pancreatic, and mammary cancer; malignant oral lesions |
| Peanut agglutinin (PNA) | Plant lectin | terminal Gal-beta1-3/4Glc/GalNAc-alpha (TF antigen) | colonic adenocarcinoma, ulderative colitis, meningiomas |
| Ricin toxin | Ricinus communis (plant) A/B plant toxin | non-reducing terminal galactose-containing glyconjugates | colon cancer cells |
| Sambucus nigra (SNA-1) | A/B plant toxin | non-reducing terminal alpha-2-6 sialic acid residues in glycoconjugates | colon cancer |
| Tetanus toxin | Clostridium tetani (bacterial) | gangliosides GT1b, GD1b, GQ1b; sialic acid containing glycoconjugates | brain and nerve tissue; melanomas |
| Ulex europeaus (UEA-I) | Plant lectin | Fuc-alpha1-2-Gal-beta1-3/4GlcNAc (blood group H/O) | vasoformative tumors (e.g. angiosarcomas) and blood vessel invasion on thyroid tumors |
| Viscumin | A/B plant toxin | non-reducing terminal galactose-containing glycoconjugates | ovarian cancer |

Those of skill in the art will recognize that the nomenclature used to designate the targeting fragment portion of a toxin molecule will differ from toxin to toxin. In one embodiment of the present invention, the targeting fragment component of the composition of the present invention is the B subunit of an A/B type toxin molecule. By "A/B type toxin molecule" we mean an oligomeric or multimeric protein where subunit B is responsible for binding at the cell surface of target cells and thus delivering the toxic A subunit to the interior of the cell.

In one embodiment of the present invention, the A/B type toxin molecule is a verotoxin molecule. The verotoxins are a family of multimeric bacteriotoxins that includes the Shiga toxin (ST) and Shiga-like toxins (SLTs). Shiga toxins are produced by the bacterium *Shigella dysenteriae* type 1, and the Shiga-like toxins are produced by various strains of *Escherchia coli*. Shiga-like toxins include types I (SLT-I) and II (SLT-II). The primary structure of SLT-I is very similar to ST, differing by a single amino acid substitution in the A subunit. The B subunits are identical. SLT-I and SLT-II share only about 56% amino acid sequence homology. SLTs specifically target intestinal cells, and production of these toxins by *E. coli* typically cause symptoms associated with food poisoning.

The A and B subunits of toxin molecules of this type each have distinct functions. The catalytic A subunit is a potent glycanase that cleaves the N-glycosidic bond at A-4324 in 28S ribosomal RNA, and thus causing inhibition of protein synthesis. The B subunit functions to deliver the A subunit to the targeted intestinal cells. The B subunit of verotoxins binds specifically to target cells by recognizing and binding to the glycosphingolipid cell surface receptor globotriaosylceramide (Gal-alpha-1-4Gal-beta-1-4Glc-Cer, or "$Gb_3$").

Subsequent to binding of the B subunit of the toxin to $Gb_3$, the entire A/B toxin molecule is internalized by the cell by endocytosis and transported to the endoplasmic reticulum. The A subunit is then translocated to the cytosol where it exerts its effect.

The A subunit of a verotoxin molecule is made up of a single A chain monomer. The B subunit is a pentamer made up of five B monomers. The B subunit monomers are capable of spontaneously assembling into an active pentamer in the absence of the A subunit. The resulting B subunit pentamer is capable of binding to the $Gb_3$ receptor and is taken up by the cell in the same manner that the intact A/B toxin would be.

Applicant has discovered that the targeting fragment of a toxin molecule is amenable to chemical modification and that the resulting chemically modified targeting fragment binds to cells possessing an appropriate cell surface receptor. In particular, applicants have discovered that the B subunit of Shiga-like toxin type 1 is amenable to chemical modification by attachment of a substance of interest and, without being bound by theory, it appears that the resulting chemically modified B subunit binds to and delivers the substance of interest to cells possessing the $Gb_3$ receptor.

By "chemical modification" of the targeting fragment we mean the association of a substance of interest to the targeting fragment to form a conjugate. The association may be covalent (e.g. the attachment of a porphyrin-type photosensitizer to an amino acid residue such as cysteine, glutamic acid or aspartic acid, or by a carbodiimide reaction to lysine residues), or non-covalent (e.g. via hydrophobic interactions), or ionic via salt bridges between charged groups on the side chains of the amino acid residues of the targeting fragment and the substance of interest. Further, the targeting fragment may be chemically modified in other ways including but not limited to the association of a visualizing agent via iodination, radiolabeling with a radioactive isotope (e.g. $I^{125}$, $Tc^{99}$, and the like), or the chelation of paramagnetic substances (e.g. gadolinium or iron oxides). Modifications may also include the association of a substance of interest by absorption. Further, the association may be of more than one form, e.g. the conjugate may be comprised of a targeting fragment with a substance of interest associated both covalently and via absorption. In addition, a single molecule or a plurality of molecules of a substance of interest may be associated with the targeting fragment. If a plurality of molecules of a substance of interest are associated with the targeting fragment, those molecules may be the same or different, i.e. a single targeting fragment may have associated with it both a photosensitizing agent and a visualizing agent. Those of skill in the art will recognize that many such modifications exist and can be utilized in the practice of the present invention. All such modifications are intended to be within the scope of present invention, so long as the resulting modified targeting fragment is capable of binding to an appropriate cell surface receptor.

The instant invention provides a composition comprising a targeting fragment of a toxin or lectin molecule and a substance of interest. In the composition, the association of the substance of interest to the targeting fragment may be of any type (covalent, ionic, absorptive, and the like). Further, the composition may be "mixed" in that the conjugates present in the composition may differ in the type of association between the targeting fragment and substance of interest. For example, the composition may be comprised of a mixture of conjugates, in some of which the association between the targeting fragment and the substance of interest is covalent, and in others of which the association is via absorption.

In other embodiments, the modification may be the "attachment" via genetic engineering of another polypeptide of interest to the targeting fragment. This type of attachment may create a chimeric protein molecule comprised of the targeting fragment moiety and at least one other polypeptide of interest. The targeting fragment and the polypeptide of interest may be translated from a single mRNA. Those of skill in the art are well acquainted with techniques for genetically engineering such chimeric proteins. Alternatively, another polypeptide of interest may be "attached" to the targeting fragment post-translationally via covalent or non-covalent (e.g. hydrophobic or ionic) means. Examples of polypeptides that could be utilized to modify the targeting fragment moiety of the conjugate include but are not limited to green fluorescent protein (GFP), including various iterations of the protein (such as those in which λ maximum of absorbance or emission has been altered, or in which various control elements or restriction sites have been introduced or removed from the coding DNA, resulting in alterations in the translated mRNA) for enhanced visualization of the targeted cells. Other examples include red fluorescent protein (Ds-Red from Clontech, Palo Alto Calif.), Vitality™ hrGFP (from Stratagene, La Jolla, Calif.), luciferase, and the like. Those of skill in the art will recognize that many polypeptides exist which could be attached to the targeting fragment in order to form a chimeric conjugate for use in the practice of the present invention. All such chimeric conjugates are intended to be encompassed by the present invention, so long as the chimera is capable of binding to an appropriate cell surface receptor.

In one embodiment of the present invention, the targeting fragment is a B subunit from Shiga-like toxin (SLTB) type 1. However, those of skill in the art will recognize that many A/B type toxin molecules exist, the B subunits of which would be suitable for use in the practice of the present invention. Examples include but are not limited to: B fragment of *Escherichia coli* heat-labile enterotoxin, B fragment of abrin, B fragment of viscumin, and B fragment of *Sambucus nigra*. Further, those of skill in the art will recognize that many modifications of a B subunit can be made for any of a variety of reasons, and that all such modified forms of the subunit may be utilized in the practice of the present invention. For example, amino acid substitutions (conservative or non-conservative), additions or deletions may be made in order to, e.g. optimize the binding affinity of the subunit for its receptor, to alter the stability or solubility of the subunit, to facilitate the construction of a chimeric conjugate, to decrease the size of the molecule in order to decrease antigenicity, or to add targeting sequences, and the like. If the B subunit is cloned into a vector, changes may be made to the nucleic acid sequence encoding the subunit in order to, for example, introduce convenient restriction sites, or to foreshorten or lengthen the coding sequence for any reason. Any such modification of a B subunit is intended to be encompassed by the term "B subunit", so long as the B subunit so modified still functions as described in the practice of the present invention.

In one embodiment of the present invention, the composition of the present invention is comprised of a targeting fragment associated with a photosensitizing agent. A "photosensitizing agent" (or "photosensitizer") is a substance that, upon exposure to light, is promoted to an excited state, and transfers its energy to a receptor molecule in the environment. The photosensitizer drops to ground state while exciting the receptor molecule. In the case of photodynamic therapy, the photosensitizer transfers energy to oxygen molecules. Oxygen in its ground state is a triplet (T), but when excited by photosensitization, is promoted to a singlet state (S). Singlet oxygen is very reactive, oxidizing membrane components in a manner that causes damage or death to living cells. The attachment of the photosensitizing agent to the targeting fragment may be carried out, for example, by absorption (i.e. through non-covalent bonds, for example, via hydrophobic interactions) or by covalent or ionic binding, or by a combination of one or more modes of association. An example of covalent binding would be the covalent attachment of the photosensitizer to the targeting fragment by a carbodiimide reaction.

In one embodiment of the present invention, the photosensitizer has a porphyrin structure. Porphyrins are cyclic conjugated tetrapyrroles such as chlorophylls and hemoglobin. In a preferred embodiment of the present invention, the porphyrin-type photosensitizer is chlorin e6 (Ce6). However, those of skill in the art will recognize that many types of photosensitizers exist that would be suitable for use in the practice of the present invention. Examples include but are not limited to: metal phtalocyanines, hypocrellins, hypericin, purpurins, furanocoumarins, chalcogenopyrylium dyes, quinolones, and the like (see Table 2).

The selection of a photosensitizing agent is based on several criteria. For example, if the targeted cells are to be illuminated in vivo, an appropriate photosensitizing agent would be one that has an absorbance wavelength maximum of at least about 600 nm in order to allow for deep penetration of the targeted tissue, e.g. a tumor mass. However, if the illumination is carried out ex vivo (as might be the case for example, in purging targeted cells from a cell sample that was to be reintroduced into the body) photosynthesizing agents with shorter absorbance maxima might be preferable. In addition, those of skill in the art will recognize that photosensitizing agents may possess multiple absorbance maxima and may thus be useful both in vivo and ex vivo. Examples of appropriate photosensitizing agents are given in Table 2.

TABLE 2

Photosensitizers and Corresponding Absorbance Wavelengths

| Photosensitizer | Type | Absorbance Wavelength Maxima (nm) |
| --- | --- | --- |
| 5-Aminolaevulinic acid (ALA) | protoporphyrin IX precursor | 400, 650 |
| Benzoporphyrin derivative monoacid ring A (BPD-MA) | porphyrin | 692 |
| Chalcogenopyrylium dyes (thio-, seleno-, telluro-pyrylium) | chalcogenopyrylium dyes | 592–675 |
| Furanocoumarines (psoralen, xanthotoxin, angelicin) | furanocoumarines | 320–360 |
| Hypocrellins A/B | perylenquinone | 658 |
| Hypericin | anthraquinone | 658 |
| Lutetium (III) texaphyrin | porphyrin | 732 |
| Malachite green | isosulphan blue derivative | 628 |
| Mono-L-aspartyl chlorin e6 | porphyrin | 664 |
| Photophrin | porphyrin | 400, 650 |
| Phthalocyanine tetrasulfonate (Zn(II) or Al(II)) | porphyrin | 672 |

TABLE 2-continued

Photosensitizers and Corresponding Absorbance Wavelengths

| Photosensitizer | Type | Absorbance Wavelength Maxima (nm) |
| --- | --- | --- |
| Quinolones (spafloxacin, lomefloxacin, enoxacin, ofloxacin, ciprofloxacin) | quinolones | 330–360 |
| Sn (IV) etiopurpurin dichloride | porphyrin | 659 |
| Temporfin (meso-tetra(m-hydroxyphenyl chlorin) | porphyrin | 652 |

The cell killing methods of the present invention are selective. The selectivity occurs on two levels. First, the ligand moiety of the conjugate binds only to specific cell surface receptors. The conjugate will not bind to cells that do not contain such specific receptors. This aspect of the invention takes advantage of the observation that many types of cancer cells over-express certain cell surface receptors, e.g. ovarian cancer cells, Burkitt's lymphoma cells, breast cancer cells, brain cancer cells, gastric cancer cells, and testicular cancer cells over-express the $Gb_3$ receptor. While it is true that some normal cells (e.g. intestinal tissue cells) also possess $Gb_3$ receptors and will therefore to a limited extent accumulate conjugate, the over-expression of $Gb_3$ in cancer cells will ensure a bias in the accumulation of the photosensitizer in cancer cells compared to normal cells. Further, the second level of specificity (described below) will attenuate the potential for damage to normal cells.

The second level of specificity is that activation of the photosensitizer (and subsequent cell damage) will occur only upon exposure to light. When the targeted cells are in vivo (i.e. located internally within the organism), they will be exposed to light only when light of an appropriate wavelength is deliberately introduced into the environment, for example, during a studied surgical procedure using, for example, optical fibers. For endoscopic use, optical fibers would be threaded through a catheter or endoscope, allowing for small incisions while delivering a focused beam of light. When the targeted cells are ex vivo, it would be possible to shield the cells until light of the wavelength that would activate the photosensitizing agent could be purposefully administered. Many companies (such as Coherent Medical Group, Coherent Inc., Palo Alto, Calif.), manufacture products specifically designed for the production of narrow wavelengths of light required for medical use. Those of skill in the art are acquainted with and will recognize that many such products exist. For example, gas lasers as well as LEDs are commercially available and capable of producing the requisite light. Any appropriate means of illuminating the target cells that results in activation of the photosensitizer molecule within the target cells, so that injury or death of the target cells results, may be utilized in the practice of the present invention. For example, of such methods of illumination, see Bellnier, D. et al. 1999.

The composition of the present invention may be administered for the purpose of selective cell killing by any of several suitable means that are well-known to those of skill in the art. For example, intramuscularly, intravenously, intratumorally, orally, and the like. Due to the intrinsic specificity of the targeting fragment of the composition, administration may be systemic. As discussed, while some cell types other than those targeted for killing may also internalize the conjugate, since they will not be exposed to light, they will not be damaged or killed. The composition may be administered in any of a variety of suitable forms, including forms that include additional components such as buffers, stabilizers, and the like, which are appropriate to the means of administration. The exact form, dosage and frequency of administration will vary from case to case and will depend on factors such as the nature and stage of the disease being treated (e.g. size and location of a tumor), characteristics of the patient (e.g. overall health, age, weight, gender and the like), and other factors such as ancillary treatments (chemotherapy, radiotherapy, and the like). The details of administration are best determined by a skilled practitioner such as a physician. Further, the details of administration are normally worked out during clinical trials. However, the approximate dosage range will be from about 0.1 to 10 mg/kg, and more preferably from about 0.25 to 1.0 mg/kg.

Likewise, the dose or frequency of illumination of the target cells will vary from case to case, but will generally be in the range of 25–200 J/cm2 light dose, 25–200 mW/cm2 fluence rate (see Ochsner, 1997, the contents of which is incorporated herein by reference in entirety).

In an ideal situation, the practice of the method of the present invention will result in the death of the targeted cells, e.g. cancer cells. However, those of skill in the art will recognize that the methods of the instant invention would also be useful even if the cancer cells were not killed outright. Other potential benefits could include attenuation of the cancer cells that would make them more susceptible to other types of cell killing such as chemotherapy or radiotherapy. (And indeed the methods of the instant invention may be practiced in conjunction with other therapeutic measures.) Similarly, abrogating or destroying the ability of the cancer cells to proliferate would also be of benefit, whether or not the cancer cells were killed outright.

The present invention encompasses methods of use of the composition of the present invention to selectively kill cancer cells. Types of cancer cells which may be selectively killed by the methods of the present invention include but are not limited to those that over-express the $Gb_3$ receptor, e.g. leukemia cells, ovarian cancer cells, Burkitt's lymphoma cells, breast cancer cells, gastric cancer cells, testicular cancer cells, and the like. The practice of the present invention may be utilized to combat cancer of any type in which the cancer cells over-express a specific cell surface receptor, and for which an appropriate targeting fragment exists that can be suitably modified by the attachment of a photosensitizing agent.

While the method of the present invention may be used for the selective killing of various types of cancer cells, other cellular populations may be targeted as well. For example, kidney, intestinal, endothelial cells, or cells infected by a pathological agent such as a virus or bacterium, may also be targeted. Any cell population characterized by the unique or biased expression of a cell surface receptor, or which can be isolated so that an appropriate wavelength of impinging light can be selectively directed to the targeted cells, and for which an appropriate targeting fragment exists that can be suitably modified by the attachment of a photosensitizing agent, may be selectively destroyed by exposure to light by the methods of the present invention.

In another embodiment of the present invention, the substance of interest is a visualizing agent. In the furtherance of this and other objectives, several different approaches could be used in concert with existing modalities to aid in the identification of cell surface receptors of interest and thus to permit visualization of, for example, tumors.

It is an objective of the present invention to facilitate nuclear scans. In the furtherance of this and other objectives, the B subunit of SLT-B is radioactively tagged for use in localizing the isotope to a tumor mass. This would allow visualization of a tumor mass using well known scintigraphic imaging techniques. It would also assist in the detection of metastatic cancer (primary tumor cells that have moved to another region of the body). Examples of currently used radioactive elements include, but are not limited to, technetium-99, iodine-125 and thallium-201. The attachment of these radioactive tracers to the B fragment can be accomplished using standard radiology chemistry techniques. The preparation and guidelines for administration of such compounds is best determined by a skilled practitioner such as a physician or radiologist (American College of Radiologist Standards, Tumor Scintigraphy-1996).

It is yet another objective of the present invention to provide a methodology suitable in X-rays or Computed Tomography scans. In the furtherance of this and other objectives, iodine or a comparable atom is used as a contrasting agent. Iodine is currently the most widely used contrast agent for X-ray and CT scans. The attachment of iodine to the B fragment will provide a positive contrast and assist in the visualization of a tumor using these two modalities Iodination of the B fragment tyrosines can be easily accomplished using well known chemistry. (Hunter and Greenwood, 1962; and Greenwood, et al., 1963). The preparation and guidelines for administration of such compounds is best determined by a skilled practitioner such as a physician or radiologist (Pediatric and Adults Thoracic Computed Tomography, American College of Radiology, standards. 1998).

It is yet another objective of the present invention is to provide a methodology in Magnetic Resonance imaging. In the furtherance of this and other objectives, paramagnetic contrast agents such as gadolinium or iron oxides are used to alter the environment of H atoms and create a contrast. Gadolinum is the most widely used contrast agent for MR imaging. Again, it is possible to attach metal complexes to the B fragment and achieve an enhancement of imaging for a tumor. The covalent attachment of gadolinium and gadolinium complexes to proteins is well known (Niemi et al., 1991; Weiner et al., 1997). The use of iron oxide nanoparticles for general contrasting purposes has been described (Schmitz et al., 1997). The preparation and guidelines for administration of such compounds is best determined by a skilled practitioner such as a physician or radiologist (Magnetic Resonance Imaging, American College of Radiology, standards. 1996)

It is yet another objective of the present invention to provide a methodology for the direct visualization of cancerous cells by complexing a fluorescent molecule to the B fragment, illuminating tissue with appropriate light and observing the light emitted. The practice of the method of the present invention would render the cancerous tissues visible and distinguishable from normal tissue. This methodology would be used during biopsy or surgical removal of a cancerous tumor. It would thus be possible to be more conservative with respect to removal of tissue that is not cancerous, thereby minimizing the loss of healthy tissue by the patient. The appropriate light sources and glasses with necessary filters for illumination and visualization are commercially available (GFP spectacles, Biological Laboratory Equipment Maintenance and Services Ltd., Budapest, Hungary). There are numerous fluorescent molecules that could be utilized in the present invention. Several characteristics of a suitable fluorescent molecule would be the excitation and emission wavelengths (Stokes radius), molar extinction coefficient, quantum yield, and chemical reactivity. Molecular Probes, (Eugene, Oreg.) specializes in the design and manufacture of fluorescent molecules for a variety of purposes. The covalent attachment of fluorophores to proteins is accomplished by commercially available chemical techniques utilizing various functional groups (amines, carboxylic acids, thiols). Sigma Chemical Co. (St. Louis, Mo.) and Molecular Probes (Eugene, Oreg.) sell such kits. The fluorescent molecule could also be proteinaceous in nature and attachment to the targeting fragment may be via the creation of a chimeric protein, as described above.

The following Examples serve to illustrate various embodiments of the instant invention.

However, they should not be construed so as to limit the invention in any way.

EXAMPLES

Materials and Methods

Materials.

Shiga-like toxin I, fragment B (SLTB) was obtained from *Vibrio cholerae* 0395 N1 containing the SLTB-encoding plasmid pSBC54. Polymyxin B nonapeptide was purchased from Sigma-Aldrich, St. Louis, Mo. Galabiose agarose resin was purchased from Calbiochem, La Jolla, Calif. Chlorin e6 (Ce6) was obtained from Porphyrin Products, Inc., Logan Utah. Fluor Link™ Cy3 reactive dye (bisfunctional NHS ester) was purchased from Amersham Pharmacia Biotech, Piscataway, N.J. MitoTracker Green FM®, Calcein AM and Ethidium homodimer-1 were purchased from Molecular Probes, Eugene Oreg. (3-(Dimethylamino) propyl)-3-ethyl-carbodiimide hydrochloride (EDC) and 1 -cyclohexyl-3(2-morpholinoethyl) carbodiimide metho-p-toluenesulfonate (CMCS) were purchased from Aldrich, Milwaukee, Wis. Sulfo-N-hydroxysuccinimide (sulfo-NHS) and Coomassie Plus Protein Reagent were obtained from Pierce, Rockford, Ill. LB media, LB agar, minimum essential media (MEM), phenol red free-DMEM/F12 (1:1)/15 mM Hepes media, fetal calf serum (FCS), penicillin, and streptomycin were purchased from Gibco BRL, Grand Island, N.Y.

Bacterial Cultures and Preparation of Periplasmic Extract.

*Vibrio cholerae* 0395 N1 (pSBC54) was plated in LB agar containing 100 µg/ml ampicillin and 100 µg/ml streptomycin, and grown overnight at 37° C. Individual colonies were picked and cultured overnight at 37° C., in 10 ml of LB media with 100 µg/ml ampicillin and 100 µg/ml streptomycin (Acheson et al., 1993). Cultures were then transferred into 1 liter of LB media/100 µg/ml ampicillin and 100 µg/ml streptomycin and incubated for 14 h at 37° C. Bacteria was pelleted by centrifuging at 5,000×g for 20 min at 4° C. The pellet was suspended in PBS and centrifuged under the same conditions. Bacterial periplasm was released by suspension of the pellet in 5 ml of 2 mg/ml polymyxin B nonapeptide/PBS, incubation for 25 min at 4° C., followed by centrifugation at 14,000×g, for 20 min at 4° C. The periplasmic extract was decanted from the bacterial pellet and stored at −70° C.

Purification of SLTB by Affinity Chromatography. SLTB was purified from the periplasmic extract by affinity chromatography on galabiose-agarose resin (2 ml of resin in 1×3 cm column).

Briefly, the galabiose agarose column was equilibrated in phospahate buffered saline (PBS)/0.02% azide. Two ml of the periplasmic extract were applied to the column and incubated for 15 min at room temperature. The column was washed with 10 ml of PBS/azide, and bound SLTB was eluted with 10 ml of 0.1 M glycine HCL, pH 2.5. To minimize denaturation of SLTB, the 0.1 M glycine fractions were collected into tubes containing neutralizing 1 M Tris. Protein content in fractions was monitored by absorbance at 280 nm. Bound fractions were pooled, dialyzed in 10 mM sodium phosphate buffer, pH 7.4 and concentrated down to 1–2 mg/ml of protein using a Centricon Plus-80 centrifugal filter device, MWCO 10,000 (Millipore, Bedford, Mass.). Purity of the bound fractions was assessed by conventional SDS polyacrylamide gel electrophoresis (SDS-PAGE). Protein concentration was measured by absorbance at 280 nm or Coomassie Plus Protein reagent.

Ce6-SLTB and Cy3-SLTB Preparations.

Cy3-SLTB conjugate—Preparation was made following manufacturer's specifications with some modifications. Briefly, to one vial of Cy3 reactive pack (1 mg), 0.4 ml of 1.8 mg/ml SLTB in 10 mM sodium phosphate buffer, pH 7.4 were added. The vial was covered with aluminum foil, and incubated overnight at room temperature in a tube rotator device. Free dye was separated from Cy3 -SLTB on a PD10 Sephadex G-25M column (Amersham Pharmacia Biotech, Piscataway, N.J.). The final protein concentration of the Cy3-SLTB conjugate was 0.17 mg/ml and the molar dye to protein ratio was 1:1.

Mixed (absorbed and covalent) Ce 6-SLTB preparations—Ce6 carboxyl groups were activated with 1-cyclohexyl-3 (2-morpholinoethyl) carbodiimide metho-p-toluenesulfonate (CMCS) and reaction of lysine residues on SLTB (Aklynina et al, 1997; Faulstich and Fiume, 1985), in a ratio of SLTB :Ce6:CMCS of(1:400:800). Briefly, 1 ml of 2 mg/ml SLTB in 10 mM sodium phosphate buffer, pH 7.4 was added to a vial containing Ce6 and CMCS. The vial with reactants was vortexed gently, wrapped with aluminum foil, and incubated overnight at room temperature in a tube rotator device. The Ce6-SLTB preparation was separated from free Ce6 by gel filtration on a G-75 Sephadex column (1.3×48 cm). Ce6 and protein were monitored by absorbance at 400 nm and 280 nm, respectively. Fractions eluting in the void volume of the column were pooled together and dialyzed against 8 liters of 10 mM sodium phosphate buffer, pH 7.5. Alternatively, Ce6 (10 mg) was derivatized with (3-(dimethylamino) propyl)-3-ethyl-carbodiimide hydrochloride (EDC) and sulfo-N-hydroxysuccinimide (sulfo-NHS) in 0.1M MES, 0.5 M NaCl, pH 6.0 (0.5 ml) (Staros et al., 1986) in the ratio of Ce6:EDC:sulfo-NHS of 1:4:2.7, for 30 minutes at room temperature, followed by addition of 1 ml of 2 mg/ml SLTB in 10 mM sodium phosphate buffer pH 7.5 and overnight incubation at room temperature in a tube rotator device. Ce6-SLTB was separated from free dye as described above. The protein concentrations of mixed Ce6-SLTB preparations were measured using Coomassie Plus Protein reagent, using as a blank a solution of free Ce6. The concentration of Ce6 in Ce-SLTB was determined by absorbance at 400 nm and 280 nm in comparison to standard curves for free Ce6 at both wavelengths. The concentration of Ce6 in the preparations was corrected for quenching by SLTB by measuring abosorbance at 400 nm and 280 nm in 5% sodium dodecyl sulphate (SDS) solutions of Ce6 and Ce6-SLTB. Quenching of absorbance of Ce6 in Ce6-SLTB was 50% at 400 nm, whereas absorbance of Ce6 at 280 nm was not affected by protein quenching. The mixed Ce6-SLTB preparations contained both Ce6 covalently linked to SLTB (Ce6-SLTB-covalent) and Ce6 absorbed to SLTB (Ce6-SLTB-absorbed). The molecular weight of the covalently bound conjugate was approximately 6.2 kD as calculated from SDS-PAGE. About 89% of total Ce6 was absorbed and 11% was covalently coupled to SLTB.

Absorbed Ce6-SLTB Preparations—Ce6 (5 mg) was mixed with 0.8 mg/ml SLTB in 10 mM sodium phosphate buffer, pH 7.4, followed by incubation overnight, in the dark, in a tube rotor device. Free Ce6 was separated from bound Ce6 to SLTB by G-75 Sephadex chromatography as described above. Excluded fractions from the G-75 chromatography were pooled together and dialyzed. Concentration of the Ce6-SLTB-absorbed conjugate was determined as described.

Cell Culture.

Wild type Vero cells (ATCC CCL 81) were cultured in minimum essential medium (MEM), containing 10% fetal calf serum (FCS), 100 units/ml of penicillin and 100 µg/ml of streptomycin. Cells were kept in a 37° C. incubator, 5% $CO_2$/air atmosphere.

Photodynamic Cell Killing

Vero cells were grown in 35 mm glass bottom gridded microwell dishes (MatTek Corp., Ashland, Mass.) to 60% confluence. Cells were washed 3 times with cold MEM media containing 0.1% bovine serum albumin (BSA) and 100 units/ml of penicillin and 100 µg/ml of streptomycin. Cells were then incubated with Ce6, Ce6-SLTB preparations (0.1–2.0 µM) in MEM/0.1% BSA/100 units/ml penicillin/100 µ/ml streptomycin at 37° C./5% $CO_2$/air for 18 h.

Before irradiation cells were washed 3 times with warm phenol red free-DMEM/F 12 (1:1)/15 mM Hepes/10% FCS/100 units/ml penicillin/100 µg/ml streptomycin and kept in the same media during irradiation. Glass bottom microwell dishes were placed in the microscope stage (Axiovert S100TV, Zeiss, Jena, Germany), with the center of the dish positioned perpendicular to the center of the condenser light (using grids on the coverslip as a guide), and irradiated with the microscope halogen lamp (100 W, 12 V, 9.8 W/mm$^2$) set at 6 V for 3 minutes. Following irradiation, cells were washed twice with warm MEM/10% FCS/100 units/ml penicillin/100 µg/ml streptomycin, and incubated in the same media for 15 minutes to 18 hours at 37° C./5% $CO_2$/air, before scoring dead/live cells.

Cell Viability Assay

The fluorescent probes calcein AM and ethidium homodimer-1 (Molecular Probes, Eugene, Oreg.) were utilized to detect the presence of live and dead cells, respectively. Calcein AM itself is non-fluorescent and permeable to membranes; it becomes fluorescent when hydrolyzed by esterases in live cells. Ethidium homodimer-1 penetrates the damaged membranes of dead cells, accumulating in the nucleus, where its fluorescence is enhanced by DNA binding. Briefly, irradiated dishes were washed 3 times with warm phenol red free-DMEM/F12 (1:1)/15 mM Hepes/0.2% BSA/100 units/ml penicillin/100 µg/ml streptomycin, followed by incubation with a solution containing 2 µM calcein AM and 4 µM ethidium homodimer-1 in the same media, for 35–45 minutes at room temperature. Fluorescence was visualized using an Axiovert S100TV inverted microscope (Zeiss, Jena, Germany), equipped with Plan-Neofluar 2.5×/0.1 NA, 5×/0.075 NA or 10×/0.3 NA objectives (Zeiss, Jena, Germany). The light source was a 50 W mercury arc lamp and excitation and emission wavelengths were selected with the filter sets HQ480/40, Q5051p, HQ 535/50 for calcein (green fluorescence); and HQ545/30, Q5701p, HQ610/75 for ethidium homodimer-1 (red fluorescence) (Chroma Technologies, Brattleboro, Vt.). Images were captured using a Roper Photometrics SenSys charged coupled device (CCD) camera (Tucson, Ariz.). The camera was controlled with IPLab software for Macintosh, Version 3.5.5 (Scanalytics, Fairfax, Va.). Live and dead cells were scored by manually counting green fluorescent cells and red fluorescent cells in captured images. Cells that were both red and green were considered dead. In addition, live and dead cells were scored by morphology changes in phase-contrast images.

Binding and Uptake Experiments

Vero cells grown on 35 mm glass bottom gridded dishes were washed 3 times with cold phenol red free-DMEM/F12 (1:1)/15 mM Hepes/0,1% BSA/100 units/ml penicillin/100 µg/ml streptomycin, and then incubated with 2 µM Ce6-SLTB or 0.04 µM Cy3-SLTB in the same media, at 4° C. for 1 hour to allow cell surface binding without protein internalization. Then, plates were washed twice with warm MEM/10% FCS/100 units/ml penicillin/100 µg/ml streptomycin and incubated at 37° C./5% $CO_2$/air for different periods of time. After each chase time, cells were washed twice with PBS and fixed with 3% formaldehyde. Zero time chase plates were washed once with cold phenol red free-DMEM/F 12 (1:1)/15 mM Hepes/10% FCS/100 units/ml penicillin/100 µg/ml streptomycin, then once with PBS, and fixed with 3% formaldehyde. Fluorescence in cells was viewed with an Axiovert S100TV inverted microscope (Zeiss, Jena, Germany) with a Plan Apochromat 63×/1.4 NA oil objective (Zeiss, Jena, Germany). The filter set D405/20X, 425DCX, E600LP (Chroma Technologies, Brattleboro, Vt.) was used for Ce6, and HQ545/30, Q5701p, HQ610/75 (Chroma Technologies, Brattleboro, Vt.) for Cy3. Images were captured as above.

Fluorescent Staining of Mitochondria

Vero cells grown on 35 mm glass bottom gridded dishes were stained with MitoTracker® Green FM, a mitochondria-specific fluorescent probe. Warm MEM/10% FCS/100 units/ml penicillin/100 µg/ml streptomycin containing 200 nM MitoTracker® Green FM was added to the dishes and incubated for 45 minutes at 37° C./5% $CO_2$/air. Cells were washed 3 times with warm phenol red free-DMEM/F12 (1:1)/15 mM Hepes/10% FCS/100 units/ml penicillin/100 µg/ml streptomycin and then observed on the microscope as described in Binding and Uptake Experiments, using the filter set HQ480/40, Q5051p, HQ 535/50. Double labeling with Ce6-SLTB and MitoTracker® Green FM were carried out by incubating cells with 2.0 µM Ce6-SLTB in MEM/0.1% BSA/100 units/ml penicillin/100 µ/ml streptomycin at 37° C./5% $CO_2$/air for 18 h. Cell were then washed three times with warm MEM/10% FCS/100 units/ml penicillin/i 100 µg/ml streptomycin and incubated with 200 nM Mitotracker® Green FM in the same media and for 45 min at 37° C./5% $CO_2$/air. Loading media was removed and the cells were washed 3 times with warm phenol red free-DMEM/F12 (1:1)/15 mM Hepes/10% FCS/100 units/ml penicillin/100 µg/ml streptomycin. Cells were viewed on the microscope as above.

Example 1

Production and Purification of SLTB

Recombinant SLTB was produced from *Vibrio cholerae* 0395 N1 transfected with the plasmid pSBC54 that encodes the gene for Shiga-like toxin I fragment B (Acheson et al, 1993). The yield of SLTB from one liter of bacterial cultures was approximately 30 mg. SLTB was purified from the periplasmic extract in a single step by affinity chromatography on galabiose-agarose as shown in FIG. 1. SDS-PAGE of the bound galabiose-agarose fraction showed a single band of about 5.6 kD molecular weight (FIG. 2) consistent with the reported molecular weight of SLTB monomer (Acheson et al, 1993). This example demonstrates that ample quantities of purified SLTB can be produced by this method.

Example 2

Characterization of Mixed Ce6-SLTB Absorbed/ Covalent Preparations by SDS-PAGE Mixed absorbed and covalently conjugated Ce6-SLTB were produced in incubations using carbodiimide activation of the carboxylic groups on Ce6 and reaction with lysine residues on SLTB as described in Material and Methods. Massively aggregated Ce6-SLTB was removed as an insoluble precipitate that remained on top of a G-75 Sephadex column. The mixed Ce6-SLTB preparation was excluded from the G-75 Sephadex column and collected in the void volume. Association of Ce6 with the mixed preparation was stable to extensive dialysis.

Figure 6A:
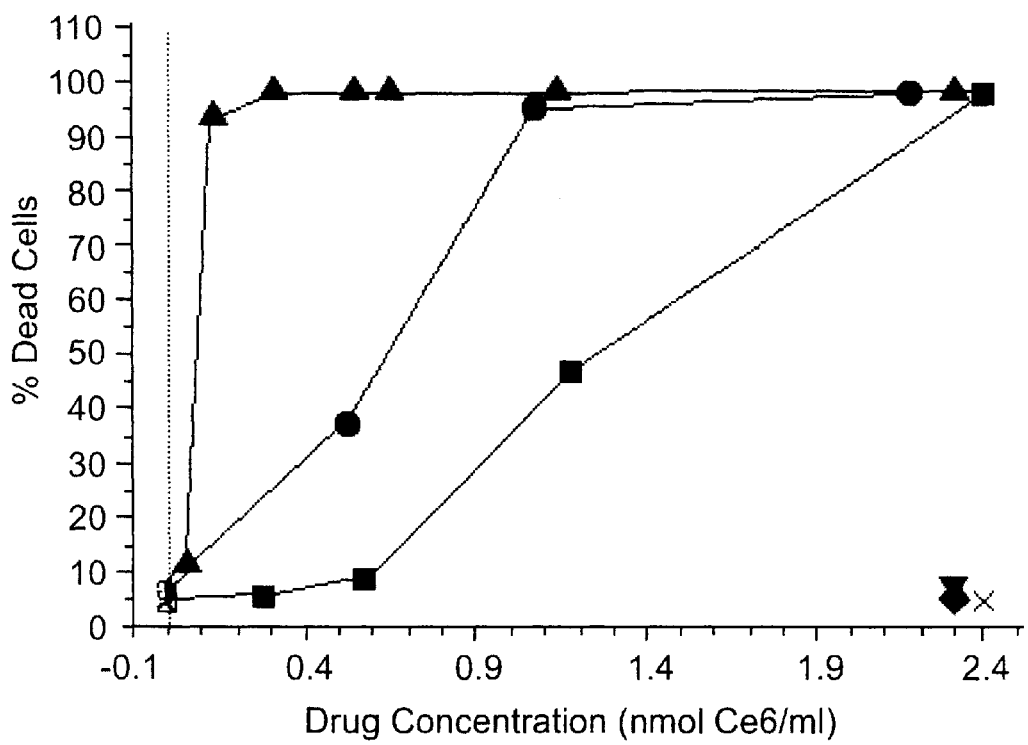
FIGS. 6A and B. Ce6-conjugate concentration dependent cell death. Vero cells grown on 35 mm glass bottom gridded dishes were incubated for 18 hours with varying concentrations of the indicated preparation, followed by irradiation as described in Material and Methods. 4 hours after irradiation, the extent of cell death was determined as described. 6A: ■=Ce6; ●=Ce6-SLTB mixed conjugate; ▲=Ce6-SLTB absorbed; X=Ce6 dark control; ◊=Ce6-SLTB mixed conjugate dark control; ▽=Ce6-SLTB absorbed dark control; ⊠=no Ce6 dark control; ○=no Ce6 illuminated control. 6B: □=Ce6-SLTB mixed conjugate; △=Ce6-SLTB absorbed.
Figure 6B:
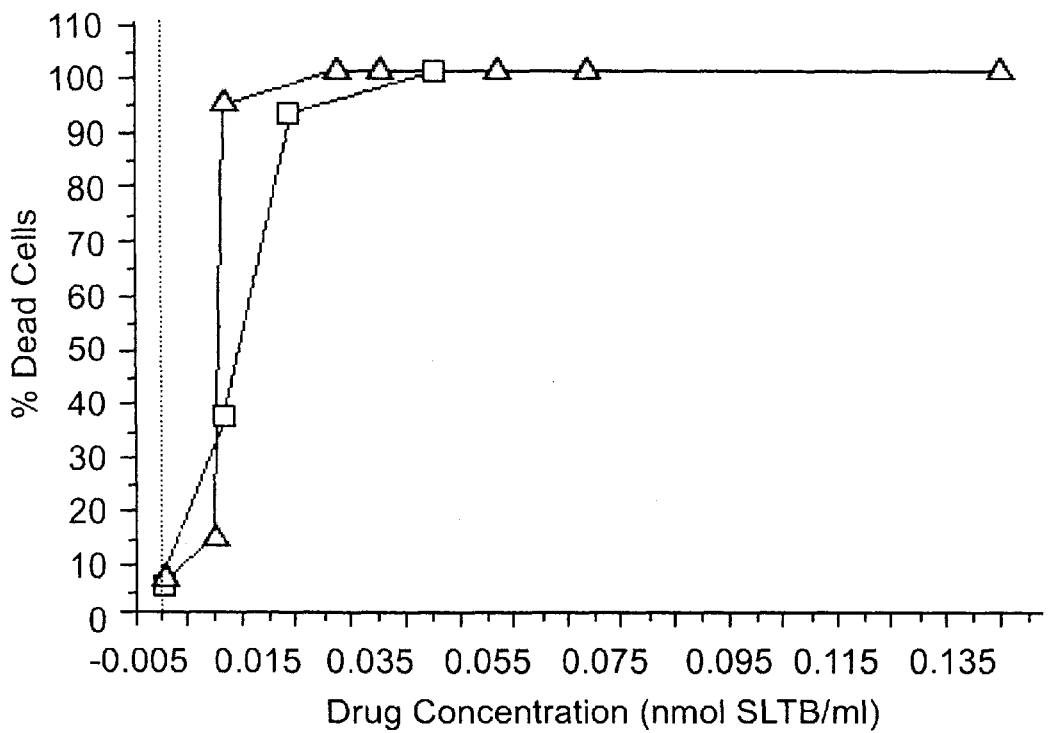
Figure 7A:
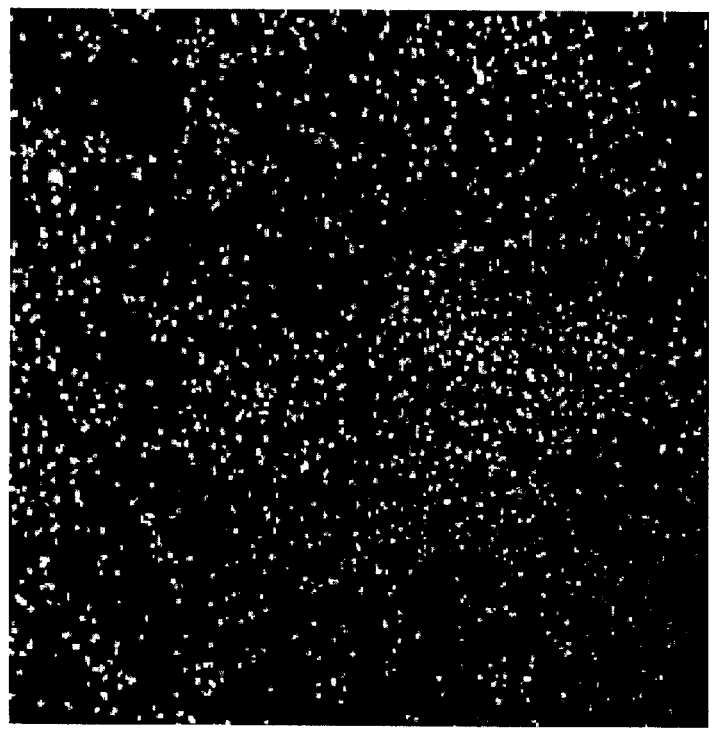
FIG. 7. Cell Killing is Restricted to Area Illuminated. Fluorescent images of dead and live Ver cells exposed to Ce6-SLTB (mixed preparation) and then irradiated. Panels A and B represent images taken at 0 hours after irradiation, and Panels C and D represent images taken 0.5 hours after irradiation. Panels A and C correspond to calcein fluorescence in live cells, and panels B and D correspond to ethidium homodimer-1 fluorescence in dead cells.
Figure 7B:
Figure 7C:
Figure 7D:
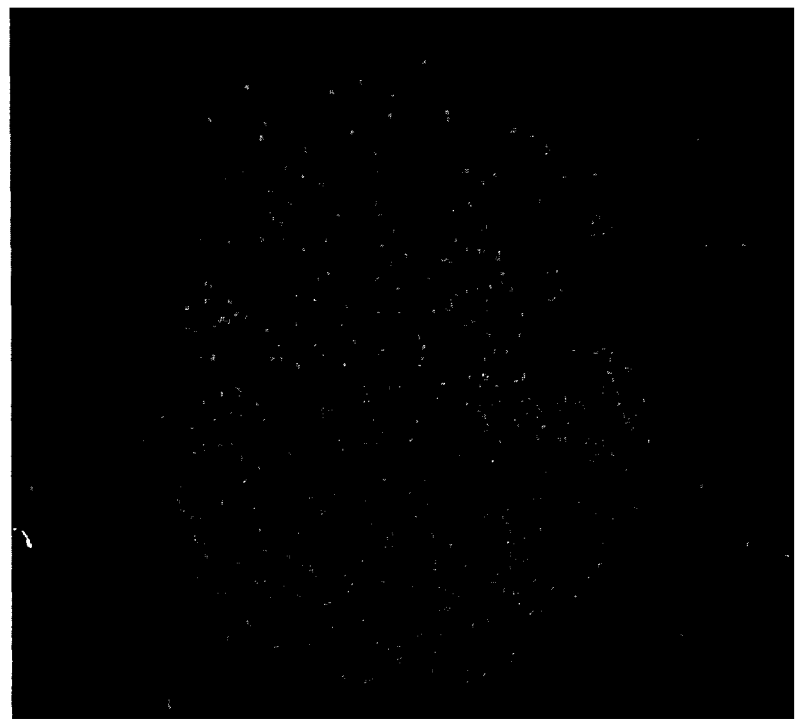
Figure 8:
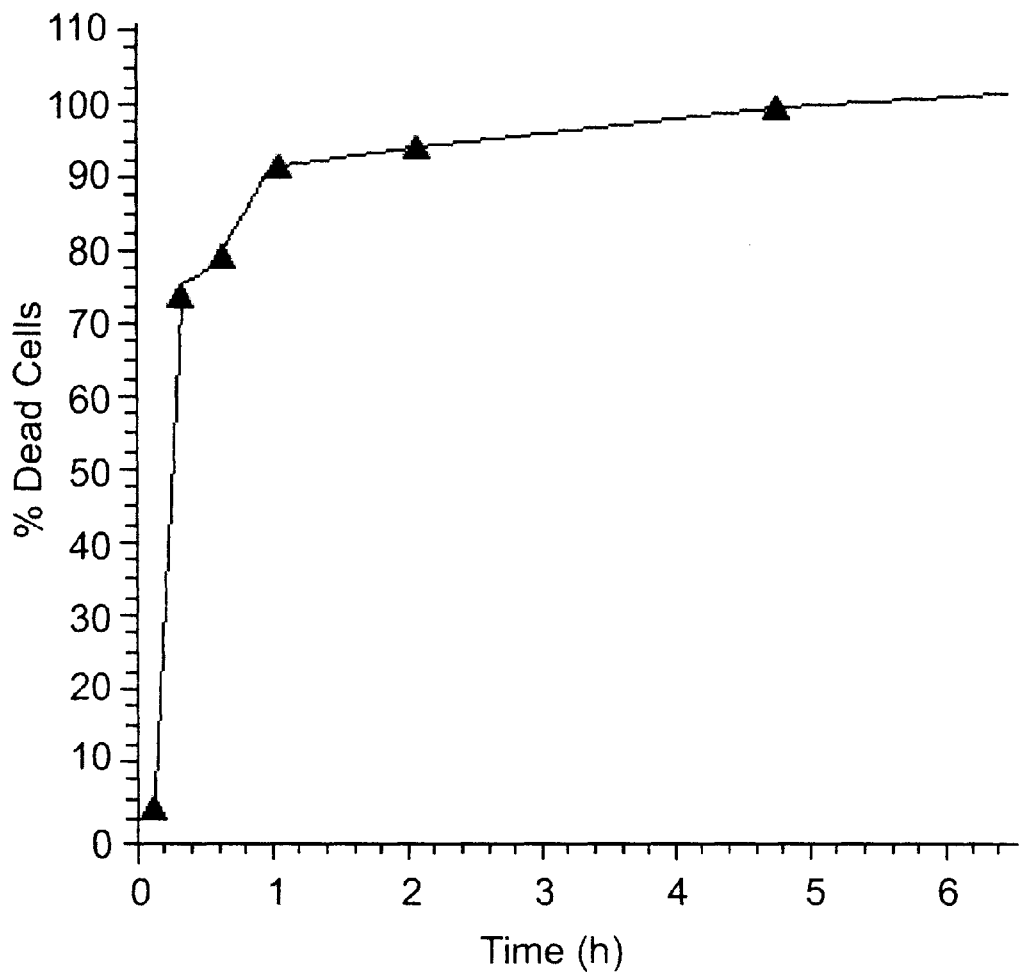
FIG. 8. Kinetics of cell killing: Quantitation of cell death by Ce6-SLTB (mixed preparation) photosensitization. Y axis is % dead cells; X axis is time in hours.

SD S-PAGE analysis of the chromatographed, dialyzed preparations indicated that they contained both absorbed Ce6 and covalently conjugated Ce6-SLT. The Ce6 from Ce6-SLTB-absorbed dissociated from SLTB during electrophoresis and ran at the "dye" front, whereas Ce6-SLT-covalent migrated as a species of about 6.2 kDa, a 0.6 kDa increase in apparent molecular weight over the starting SLTB (data not shown). Based on Ce6 intensities in SDS-PAGE gels, 89% of the Ce6 in the mixture was present as absorbed Ce6-SLTB, and 11% of the Ce6 was present as covalent Ce6-SLTB.

Example 3

Delivery of Ce6 to Targeted Cells by Ce6-SLTB Conjugates

Experiments were carried out in which the ability of Ce6-SLTB preparations to promote the delivery of Ce6 to targeted cells was assayed. Vero cells were incubated at 4° C. with either free Ce6 or mixed (absorbed and covalent) Ce6-SLTB preparations (equal quantities of Ce6 in both). The results showed that when cells were incubated with mixed Ce6-SLTB preparations, cell-associated Ce6-specific fluorescence was readily detected (FIG. 3). In contrast, cells incubated with free Ce6 under the same conditions showed no detectable Ce6-specific fluorescence (data not shown), indicating that the presence of SLTB was essential for the association of Ce6 fluorescence with the targeted cells.

Example 4

Comparative Binding and Uptake of Cy3-SLTB and Mixed Ce6-SLTB Preparations

Cy3 conjugated SLTB is an accepted covalent tracer for the binding and intracellular internalization of SLTB protein (Johannes et al, 1997; Girod et al., 1999). Binding of Cy3-SLTB at 4° C. to Vero cells gave a rim staining pattern about the edge of individual cells, staining typical of SLTB binding to its cell surface receptor (FIG. 4, 0h) Chase of the cell surface bound Cy3-SLTB for 1–18 hour at 37° C resulted a pattern of fluorescence consistent with retrograde transport of Cy3-SLTB from the plasma membrane to the Golgi apparatus (GA) and to the endoplasmic reticulum (ER) as reported elsewhere (Johannes et al., 1997; Girod et al., 1999). Retrograde transport is the process by which endocytic vesicles containing surface receptor and bound toxin are transported from early endosomes all the way to the Golgi and then to the endoplasmic reticulum. FIG. 4 shows photographs of the Vero cells after 0, 1, 4, and 18 hours of chase. This pattern of uptake and distribution is indicative of receptor-mediated endocytosis.

In contrast, at 4° C. Ce6-SLTB mixed conjugate showed little surface binding to Vero cells as evidenced by a lack of edge staining of the cells, and instead showed fluorescence staining over the entire cell body (FIG. 3). Chasing of mixed Ce6-SLTB at 37° C. from 1–18 hours resulted in a distinct change in the character of the Ce6 staining inside the cells. Fluorescence inside Vero cells increased, and it appeared to be more localized in thick, tubular organelle structures that resembled mitochondria. Photographs taken at 0, 1, 2, and 4 hours of chase are depicted in FIG. 3.

This pattern of uptake and distribution is not indicative of receptor mediated endocytosis, but rather would be consistent with passive diffusion of Ce6 across the plasma membrane and into the interior of the cell. This observation is likely the result of binding of the Ce6-SLTB-absorbed species to the $Gb_3$ receptor, followed by release of the Ce6 into the plasma membrane and entry of the Ce6 into the cell via passive diffusion across the membrane.

This example demonstrates that SLTB functions as an efficient means to transport a photosensitizing agent into the cytoplasm of cells.

Example 5

Mixed Ce6-SLTB Preparation Distribution in Vero Cells

In order to determine if Ce6 was accumulating in mitochondria, double labeling experiments were carried out in which Vero cells were simultaneously labeled with the green fluorescent mitochondria marker, MitoTracker® Green FM and exposed to mixed Ce6-SLTB. The pattern of green fluorescence resulting from MitoTracker® Green FM labeling (FIG. 5A) and the pattern of red fluorescence resulting from the accumulation of Ce6 (FIG. 5B) was determined, and an overlay comparison of the two (red and green) fluorescence patterns was carried out. The comparison showed that most of the Ce6 co-localized with MitoTracker® Green FM in mitochondria. This observation is consistent with passive diffusion of the Ce-6 across the plasma membrane, suggesting that the source of the Ce6 in mitochondria may be from the Ce6-SLTB-absorbed conjugate species.

However, Ce6 red fluorescence was also observed, albeit to a lesser extent, in the GA and ER of the cells. This is most likely due to the entry of some Ce6 into the cell by receptor mediated endocytosis, consistent with the delivery of Ce6 to the cells by the (approximately 11%) Ce6-SLTB conjugate in which the Ce6 is covalently bound.

Thus, the nature of the association of Ce6 with SLTB (covalent or absorptive) appears to determine the final destination of Ce6 inside the cell. Ce6 absorbed to SLTB appears to accumulate in mitochondria, whereas Ce6 covalently linked SLTB localizes in the GA and ER of the cells, and at the cell surface.

Example 6

Comparison of Mixed-Ce6-SLTB-preparation, Absorbed-Ce6-SLTB and Free Ce6 Dependent Photodynamic Cell Killing Vero cells were treated with varying concentrations of free Ce6, mixed-Ce6-SLTB preparation, and absorbed-Ce6-SLTB, followed by irradiation with a halogen lamp as described in MATERIAL AND METHODS. The results of this experiment, presented in FIG. 6A, showed that both mixed Ce6-SLTB preparations and absorbed-Ce6-SLTB are significantly more efficient at photodynamic cell killing than free Ce6. Expressed in molar concentration of Ce6, the LD50 for absorbed Ce6-SLTB was 0.1 nmol/ml, the LD50 for mixed Ce6-SLTB was 0.6 nmol/ml, and the LD50 of free Ce6 was 1.2 nmol/ml. Plotting cell death versus SLTB concentration (FIG. 6B) showed that, at the same protein concentration (0.015 µM), both mixed Ce6-SLTB-conjugate and absorbed Ce6-SLTB produced the same degree of cell death.

These results clearly demonstrate that both mixed Ce6-SLTB preparations and absorbed-Ce6-SLTB are significantly more efficient at photodynamic cell killing than free Ce6. Further, these results confirm that the targeting (B) fragment of Shiga-like toxin type 1 is an effective vehicle for delivering a substance of interest, such as a photosensitizer, to cells containing the $Gb_3$ cell surface receptor.

Example 7

Localization and Kinetics of Cell Killing With Mixed Ce6-SLTB-Preparation

The localization of cell killing by mixed Ce6-SLTB was investigated by calcein and ethidium homodimer-1 fluorescence. Calcein fluorescence occurs only in live cells, whereas ethidium homodimer-1 fluorescence occurs only in dead cells. The results are depicted in FIG. 7, panels A–D, where panels A and C correspond to calcein fluorescence at 0 and 0.5 hours after irradiation, respectively, and panels B and D correspond to ethidium homodimer-1 fluorescence at 0 and 0.5 hours after irradiation, respectively. As can be seen in Panel A, cells exposed to the Ce6-SLTB preparation display readily detectable calcein fluorescence immediately after irradiation (0 hours), i.e. they are alive. However, as can be seen in Panel C, 0.5 hours after irradiation few living cells remain within the central, circular area of the field that was irradiated, whereas the remaining non-irradiated area is still populated by living cells. Likewise, ethidium homodimer-1 fluorescence of Ce6-SLTB exposed cells shows essentially no dead cells immediately after irradiation (0 hours, Panel B). However, 0.5 hours after irradiation (Panel D), the circular area of the field that was irradiated (and only the circular irradiated area) contains many dead cells. This demonstrates that the killing of cells exposed to Ce6-SLTB is confined to only those cells which are exposed to light. Cells which are not exposed to light are not affected.

In order to determine the rate of cell killing after mixed Ce6-SLTB-preparation treatment and irradiation of Vero cells, cell death (as indicated by the percentage of dead cells) was assessed at times ranging from 0–18 hours post-irradiation. The results showed that extensive cell death was evident as soon as 0.25 hours after irradiation. Quantitation of the data (FIG. 6) revealed greater than 70% cell death only 0.25 hours after irradiation, and close to 95% cell death two hours after irradiation. After 5 hours post-irradiation, cell death was essentially 100% and dead cells were observed to detach from the dish.

This example demonstrates that treatment of cells with a mixed Ce6-SLTB-preparation followed by irradiation is a rapid and effective method of cell killing.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

References

Acheson, D. W. A., Calderwood, S. B., Boyko, S. A., Lincicome, L. L., Kane, A. V., Donohue-Rolfe, A., and Keush, G. T. 1993. Comparison of Shiga-Like Toxin I B-Subunit Expression and Localization in *Echrichia coil* and *Vibrio cholerae* by Using trc or Iron-Regulated Promoter Systems. *Infection and Immunity,* 61: 1098–1104.

Aklynina, T. V., Jans, D. A., Rosenkranz, A. A., Statsyuk, N. V., Balashova, I. Y., Toth, G., Pavo, I., Rubin, A. B., and Sobolev, A. S. 1997. Nuclear Targeting of Chlorin e6 Enhances its Photosensitizing Activity. *Journal of biological Chemistry.* 272: 20328–20331.

Bellnier, D. et al. 1999. Design and construction of a light-delivery system for photodynamic therapy. *Med. Phys.* 26: 1552.

Faulstich, Hl and Fiume, L. 1985. Protein Conjugates of Fungal Toxins. *Methods in Enzymology,* 112: 225–237.

Girod A., Storrie, B., Simpson, J. C., Johannes, L. Goud, B., Roberts, L. M., Lord, J. M., Nilsson, T., and Pepperkok, R. Evidence for a COP-I-independent transport route from the Golgi complex to the endoplasmic reticulum. *Nature Cell Biology,* 1: 423–430. 1999.

Greenwood, F. C., Hunter, W. M. and Glover, J. S., 1963. *Biochemical Journal,* 89, 114–23.

Hunter, W. M. and Greenwood, F. C., 1962. *Nature,* 194, 495–6.

Johannes, L., Tenza, D., Antony, C., and Goud, B. 1997. Retrograde transport of KDEL-bearing B fragment of Shiga toxin. *Journal of biological Chemistry,* 272, 19554–19561.

Kilpatrick, D. C. 2000. Introduction to Animal Lectins. In: *Handbook of Animal Lectins: Properties and Biomedical Applications,* pp. 1–10. J. Wiley and Sons, LTD, Chichester, England.

Niemi et al., 1991. *Investigative Radiology* 26:7, 674–80.

Ochsner, M. 1997. Photodynamic Therapy: the Clinical Perspective. Review on applications for control of diverse tumours and non-tumour diseases. *Drug Res.,* 47:1185–1194.

Schmitz et al. 1997. *Investigative Radiology* 35:8, 460–71.

Staros, J. V., Wright, R. W. and Swingle, D. M. 1986. Enhancement by N-hydroxysulfosuccinimie of water-soluble carbodiimide-mediated coupling reaction. *Analytical Chemistry,* 156: 220–222.

Weiner et al., 1997. *Investigative Radiology* 35:8, 460–71.

We claim:

1. A method for identifying a cell surface receptor of interest in patients and clinical samples, comprising the steps of
   a) providing to said patients or clinical samples a composition comprising a targeting fragment of a toxin or lectin molecule and a visualizing agent, wherein said visualizing agent is selected from the group consisting of an X-ray/CT contrast agent, and MRI contrast agent, a fluorescent molecule and a fluorescent protein; and
   b) locating said cell surface receptor in said patient or clinical sample by imaging said visualizing agent after said targeting fragment of said toxin has bound to said cell surface receptor.

2. The method of claim 1 wherein said visualizing agent is an X-ray/CT contrast agent.

3. The method of claim 2 wherein said X-ray/CT contrast agent is iodine.

4. The method of claim 1 wherein said visualizing agent is an MRI contrast agent.

5. The method of claim 4 wherein said MRI contrast agent is selected from the group consisting of a paramagnetic atom and a paramagnetic compound.

6. The method of claim 5 wherein said paramagnetic atom is gadolinum.

7. The method of claim 5 wherein said paramagnetic compound is iron oxide.

8. The method of claim 1 wherein said visualizing agent is selected from the group consisting of a fluorescent molecule and a fluorescent protein.

9. A method for identifying a cell surface receptor of interest in patients and clinical samples, comprising the steps of
   a) providing to said patients or clinical samples a composition comprising a targeting fragment of a toxin or lectin molecule and a visualizing agent; and
   b) locating said cell surface receptor in said patient or clinical sample by imaging said visualizing agent after said targeting fragment of said toxin has bound to said cell surface receptor, wherein said targeting fragment of a toxin or lectin molecule is a B fragment of an A/B type toxin molecule.

10. The method of claim 9 wherein said B fragment of an A/B type toxin molecule is selected from the group consisting of B fragment of Shiga-like toxin type-1, B fragment of *Escherichia coli* heat-labile enterotoxin, B fragment of abrin, B fragment of viscumin, and B fragment of *Sambucus nigra*.

11. A method of claim 9 wherein said visualizing agent is an X-ray/CT contrast agent.

12. The method of claim 9 wherein said visualizing agent is an MRI contrast agent.

13. The method of claim 9 wherein said visualizing agent is selected from the group consisting of a fluorescent molecule and a fluorescent protein.

14. A method for identifying a cell surface receptor of interest in patients and clinical samples, comprising the steps of
   a) providing to said patients or clinical samples a composition comprising a targeting fragment of a toxin or lectin molecule and a visualizing agent; and
   b) locating said cell surface receptor in said patient or clinical sample by imaging said visualizing agent after said targeting fragment of said toxin has bound to said cell surface receptor, wherein said cell surface receptor is selected from the group consisting of $Gb_3$ GM1, GM2, Gd1b, GT1b, TF antigen, non-reducing terminal galactose, N-acetylgalactosamine, alpha 2-6 sialic acid, and alpha 1-2 fucose containing glycoconjugates.

* * * * *